United States Patent
Istar

(10) Patent No.: US 6,600,806 B1
(45) Date of Patent: Jul. 29, 2003

(54) SYSTEM FOR RADIOGRAPHIC DETERMINATION OF PIPE WALL THICKNESS

(75) Inventor: Ata Istar, Gaithersburgh, MD (US)

(73) Assignee: Rochester Gasand Electric Corporation, Rochester, NY (US)

(*) Notice: Subject to any disclaimer, the term of this patent is extended or adjusted under 35 U.S.C. 154(b) by 37 days.

(21) Appl. No.: 09/585,856

(22) Filed: Jun. 1, 2000

Related U.S. Application Data

(60) Provisional application No. 60/137,067, filed on Jun. 2, 1999.

(51) Int. Cl.[7] .............................................. G01B 15/06
(52) U.S. Cl. ........................................... 378/59; 378/58
(58) Field of Search ...................... 378/58, 59

(56) References Cited

U.S. PATENT DOCUMENTS

| | | | |
|---|---|---|---|
| 3,770,959 A | * 11/1973 | Gloor et al. ................... | 378/58 |
| 4,187,425 A | * 2/1980 | Thompson .................... | 378/59 |
| 4,330,835 A | * 5/1982 | Ghem ........................ | 702/172 |
| 4,393,305 A | * 7/1983 | Shimizu et al. ........... | 250/358.1 |
| 4,590,658 A | * 5/1986 | Funyu et al. .................. | 29/464 |
| 4,644,574 A | * 2/1987 | Dahn .......................... | 378/58 |
| 4,692,936 A | 9/1987 | Billeaudeaux ............... | 378/59 |
| 4,695,729 A | * 9/1987 | Monno et al. ........... | 250/358.1 |
| 4,725,963 A | * 2/1988 | Taylor et al. ................. | 702/40 |
| 4,857,736 A | * 8/1989 | Long ..................... | 250/358.1 |
| 4,974,246 A | 11/1990 | Heiskel ......... | 378/59 |
| 5,138,644 A | * 8/1992 | McArdle et al. ............. | 378/55 |
| 5,614,720 A | 3/1997 | Morgan et al. .......... | 250/360.1 |
| 5,864,601 A | 1/1999 | Cattorini et al. .............. | 378/59 |
| 5,931,795 A | * 8/1999 | Manly et al. ................ | 600/587 |
| 6,229,872 B1 | * 5/2001 | Amos .......................... | 378/58 |
| 6,240,160 B1 | * 5/2001 | Daaland et al. ............... | 378/59 |
| 6,377,654 B1 | * 4/2002 | Willems et al. ............... | 378/59 |

* cited by examiner

*Primary Examiner*—Robert H. Kim
*Assistant Examiner*—Allen C Ho
(74) *Attorney, Agent, or Firm*—Neal L. Slifkin; Harris Beach LLP

(57) ABSTRACT

A system for determining pipe wall thickness includes a supporting framework removably attachable to the outer surface of a pipe or pipe covering and supportive of an x-ray film holder. The holder and an x-radiation source are disposed on opposite sides of the pipe in a first plane which includes the axis of the pipe. The source may be moved along the axial plane to make successive exposures of the pipe on a single piece of film. Each image includes both the upper-and lower side walls of the pipe. The film holder may be radially indexed to the pipe on the supporting framework so that the film holder and source may be disposed successively in a plurality of other axial planes radially displaced from the first axial plane. For each plane, a fresh piece of film is installed in the holder. After processing of all films, the pipe side wall thicknesses may be inferred for each axial and radial location by direct measurement of the film images, providing a substantially three-dimensional display of wall thickness of the pipe. Thickness data from the radiographs may be entered readily into any of various well known commercial software programs for computer analysis if so desired. At each axial position of the supporting framework, the exact locations of the clamping feet may be inscribed on the pipe or pipe covering so that later determinations may be made from exactly the same locations, thus permitting precise monitoring of pipe wall thickness over time.

4 Claims, 12 Drawing Sheets

| Pipe Size | NSAC Grid Size | Number of Films | Angle of Films | Resulting Grid Size |
|---|---|---|---|---|
| 2" | 1.00" | 4 | 0°,45°,90°,135° | 0.93" |
| 3" | 1.00" | 6 | 0°,30°,60°,90°,120°,150° | 0.92" |
| 4" | 1.17" | 6 | 0°,30°,60°,90°,120°,150° | 1.17" |
| 6" | 1.73" | 6 | 0°,30°,60°,90°,120°,150° | 1.73" |

FIG. 9

| Degree Measure | 4 Films | 6 Films |
|---|---|---|
| 0° | A,E | A,G |
| 30° | -- | B,H |
| 45° | B,F | -- |
| 60° | -- | C,I |
| 90° | C,G | D,J |
| 120° | -- | E,K |
| 135° | D,H | -- |
| 150° | -- | L,F |

FIG. 10

SYSTEM FOR RADIOGRAPHIC DETERMINATION OF PIPE WALL THICKNESS

The present application is a conversion of a US Provisional Application, Ser. No. 60/137,067, filed Jun. 2, 1999, and claims that priority date.

BACKGROUND OF THE INVENTION

1. Field of the Invention

The present invention relates to systems for determining wall thicknesses along a length of closed pipe such as a pipeline in an industrial installation; more particularly, to such a system using photographic images of x-ray exposures to infer such wall thicknesses; and most particularly, to such a system wherein the film and the x-ray source are sequentially and accurately positioned at a predetermined array of axial and radial locations to provide a three-dimensional assessment of pipe wall thickness over a predetermined length of pipe.

2. Discussion of the Related Art

Pipelines in many industrial applications are subject to internal corrosion over time. Such pipelines may carry hazardous materials and may be operated at elevated temperatures and/or pressures. Thus, the thickness of the pipe wall can be a critical safety consideration, and accurate determination of remaining wall thickness can be an important part of a maintenance and safety program.

In general, such pipelines are closed and filled with the working materials; thus, it is impractical to make direct physical inspections and measurements of wall thickness. Various inferential techniques have been applied. One commonly employed technology involves ultrasonic measurement, but this typically requires that any pipe covering such as insulation be removed and a smooth surface be ground oh the pipe exterior for coupling of an ultrasonic horn, and further, that the pipe be emptied. Thus, ultrasonics generally cannot be applied to a pipeline in service.

Numerous systems involving radiography have been proposed. Such systems generally have a radiation source, typically gamma rays or x-rays, disposed adjacent a front wall portion of a pipe; and sensing means, such as photographic film or electronic receptors, disposed adjacent the back wall portion of the pipe, opposite the front wall portion. For purposes of the following discussion, the pipe, although typically cylindrical, may be thought of as having left and right side wall portions, respectively, for a vertical pipe, corresponding to upper and lower side wall portions for a horizontal pipe, connecting the front and back wall portions, although the limits of any wall portion of a cylindrical form cannot be strictly defined.

U.S. Pat. No. 4,692,936, issued Sep. 8, 1987 to Billeaudeaux, discloses a radiation source off-spaced from the front wall of a pipe and a flat photographic film disposed behind the pipe. The apparatus further includes a comparative scale body constructed of brass and having a range of known thicknesses. The step-scale body is radiographed adjacent to and simultaneously with the pipe portion of interest, and the thickness of the pipe wall may be inferred from the radiograph by comparing the wall image with the scale body image.

U.S. Pat. No. 4,974,246, issued Nov. 27, 1990 to Heiskel, discloses a radiation source and film in the conventional relationship except that they are separated axially along the pipe such that the centerline of the radiation forms an incident angle with the pipe of between 30° and 75°. This system is said to be useful in checking for internal pipe corrosion at hangers or supports where orthogonal radiography is impractical.

U.S. Pat. No. 5,614,720, issued Mar. 25, 1997 to Morgan et al., discloses an apparatus having a scannable radiation source off-spaced from the front wall of the pipe and a semicircular array of radiation receptors disposed around the back half of the pipe. The electronic receptors provide an array of signals which are collected and analyzed by a computer alogrithm to determine deviations from the expected thickness of the pipe at a variety of radial angles. The apparatus may be moved around the pipe as well as along the pipe to make multiple determinations which can be combined by the algorithm to provide a model of the wall thickness both radially and axially of the pipe.

U.S. Pat. No. 5,864,601,. issued Jan. 26, 1999 to Cattorini et al., discloses a conventional arrangement between radiation source and photographic film. Two shims of different thickness are placed adjacent an area of suspected corrosion in the back wall of the pipe and are radiographed therewith. Thickness of the corroded area is inferred by computer analysis of optical density data from the shim and pipe back wall images.

In general, the prior art approaches use optical density analysis to infer thickness of portions of the back wall of a pipe. of the just-discussed patents, only U.S. Pat. No. 4,692,936 discloses apparatus and method for determining pipe wall thickness by measuring directly the radiation shadow of the side wall, as shown in that patent's FIGS. 3 and 4. But this disclosure makes no provision. for sytematically examining closely-spaced portions of a pipe, both radially and axially, and for repeatedly making such examination with-a high degree of accuracy to monitor the progress of corrosion therein over time.

What is needed is a simple yet reliable system for measuring optically, by radiography and subsequent trigonometry, both apparent and true wall thickness of a pipe at a predetermined array of radial and axial positions, and for being able to repeat such measurements at each of such positions at any desired intervals of time, wherein the pipe may be under operating conditions at the time of measurement.

SUMMARY OF THE INVENTION

It is a principal object of the invention to provide an improved system for radiographically determining the wall thickness of a pipe at any desired location.

It is a further object of the invention to provide an improved system for radiographically determining the wall thickness of a pipe at any desired location relative to other wall thicknesses at other radial and/or axial pipe locations.

It is a still further object of the invention to provide an improved system for monitoring the progress over time of wall thinning of a pipe in service at any desired radial or axial location along the pipe.

BRIEF DESCRIPTION OF THE INVENTION

Briefly described, a system in accordance with the invention includes a supporting framework removably attachable to the outer surface of a pipe or pipe covering and supportive of a holder for photographic film for recording x-radiation from an x-ray source off-spaced from the holder. The holder and the source are disposed on opposite sides of the pipe in a first plane which, includes the axis of the pipe. The source is axially movable so that successive exposures may be made of the pipe along the first axial plane on a single piece of film or successive films. Each such image preferably includes both the upper and lower side walls of the pipe. The film holder is also radially indexable to the pipe via a plurality of regularly-spaced radial bores in arcuate end pieces of the supporting framework, so that the film holder and source may be disposed successively in a plurality of other axial planes radially displaced from the first axial plane.

In each such plane, a fresh piece of film is installed in the holder. After processing of all films, the pipe side wall thicknesses may be determined for each axial and radial location by measurement of the film images, thereby providing a substantially three-dimensional display of wall thickness of the pipe over the axial length of the film exposures made. Thickness data from the radiographs may be entered readily into any of various well known commercial software programs for computer analysis if so desired. At each axial position of the supporting framework, the exact locations of the clamping feet may be inscribed on the pipe or pipe covering, such that later determinations may be made from exactly the same locations, thus permitting precise monitoring of pipe wall thickness over time.

BRIEF DESCRIPTION OF THE DRAWINGS

The foregoing and other objects, features, and advantages of the invention, as well as presently preferred embodiments thereof, will become more apparent from a reading of the following description in connection with the accompanying drawings in which:

FIG. 5 is a rear elevational view of a film holder shown in

FIG. 9 is a table relating pipe diameter to the number of films and number of radial filming angles needed to meet the NSAC pipe inspection standard;

FIG. 10 is a table showing the radial positions and pipe positions imageable with four films and with six films;

DETAILED DESCRIPTION OF THE INVENTION

Figure 1:
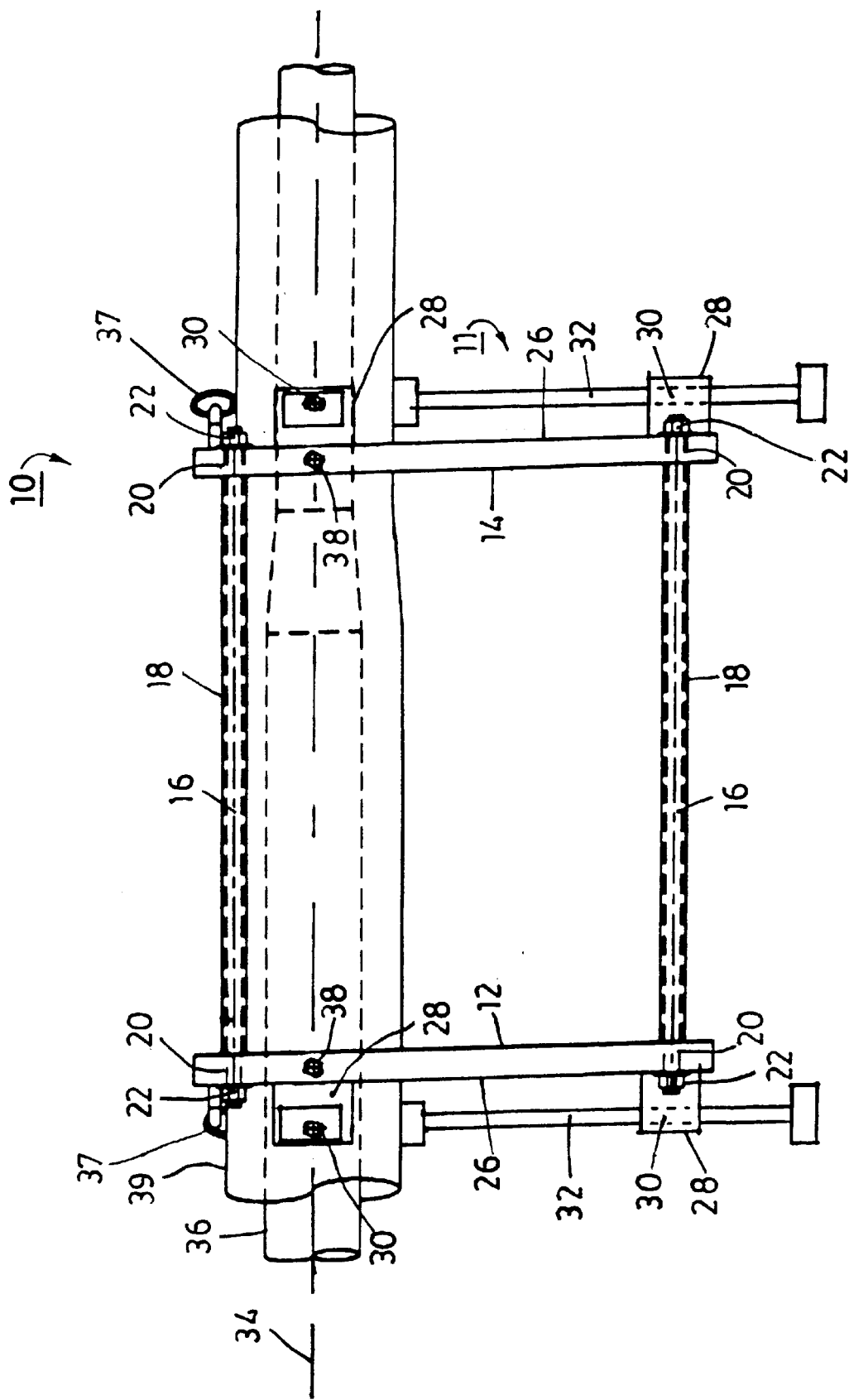
FIG. 1 is a front elevational view of a supporting framework in accordance with the invention, shown mounted for operation on a pipe having an insulative covering.

The invention is directed to means for accurately and repeatably positioning an x-ray sensitive photographic film on side of a pipe for recording x-radiation from an off-spaced x-ray source on the other side of the pipe, the source being movable axially of the pipe, and the source and film being movable radially of the pipe, to obtain a cylindrical mosaic of pipe side wall thicknesses.

Referring to FIGS. 1 through 7, a system 10 in accordance with the invention has a supporting-framework 11 including first and second arcuate end pieces 12,14 rigidly connected in plane-parallel and off-spaced relationship by connecting rods 16 passing through tubular spacers 18 between end pieces 12,14 and through bores 20 in the spacers and secured by nuts 22.

Figure 2:
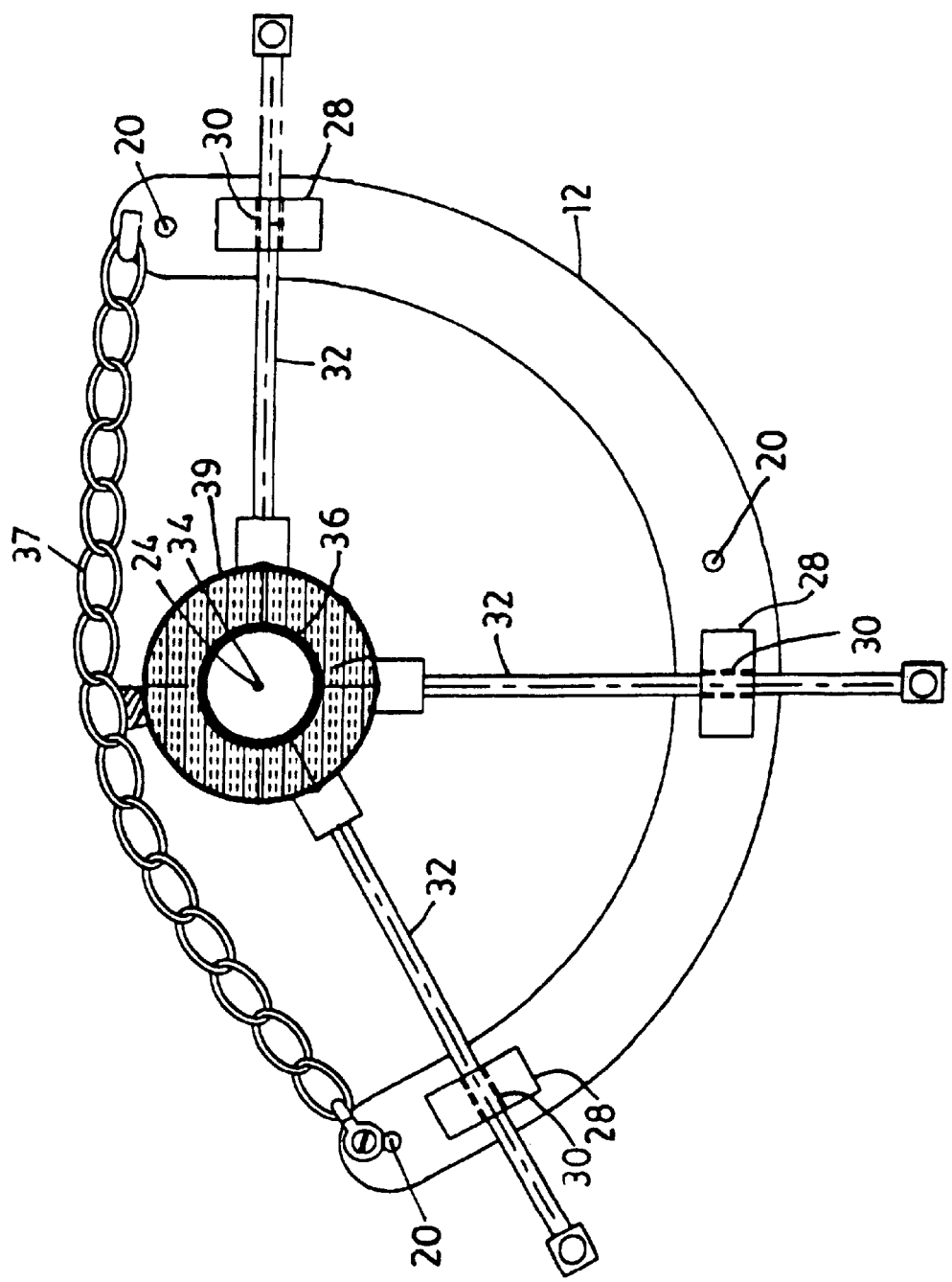
FIG. 2 is an end view from the left side of the supportive framework as shown in FIG.1.
Figure 3:
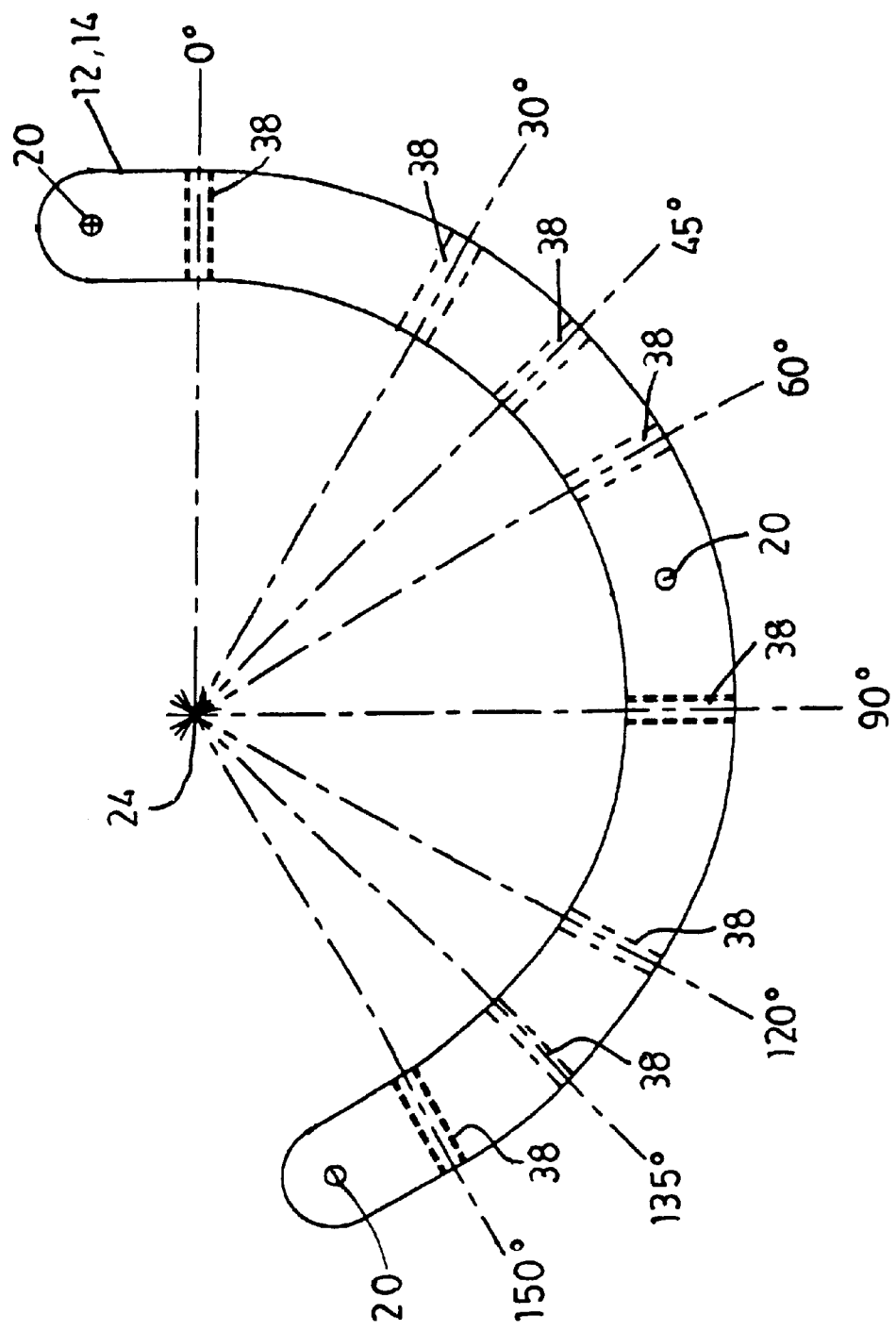
FIG. 3 is a cross-sectional view of an end piece of the supporting framework shown in FIG. 1, showing the angles of radial bores therethrough.

Preferably, the arcs of spacers 12,14 are centered on axis 24 of supporting framework 11, as shown in FIG. 3. Each spacer is provided on its outboard side 26 with a plurality of mounting blocks 28 disposed preferably at 90° and 135°, respectively as shown in FIG. 2. Each mounting block 28 has a threaded radial bore 30 therethrough for receiving a threaded positioning screw 32. The screws are radially adjustable in the mounting blocks to bring axis 24 of arcs 12 into coincidence with axis 34 of pipe 36, as shown in FIG. 2. Such coincidence is important, because each of end pieces 12,14 is further provided with an array of threaded radial bores 38, preferably eight, disposed at radial angles between 0° and 150°, as shown in FIG. 3. When axes 24 and 34 are coincident, the axes of bores 38 are desirably coincident with radii of pipe 36. Framework 11 may be shackled and retained on pipe 36 by any convenient restraint, for example, lanyards, cables, or chains 37.

Figure 4:
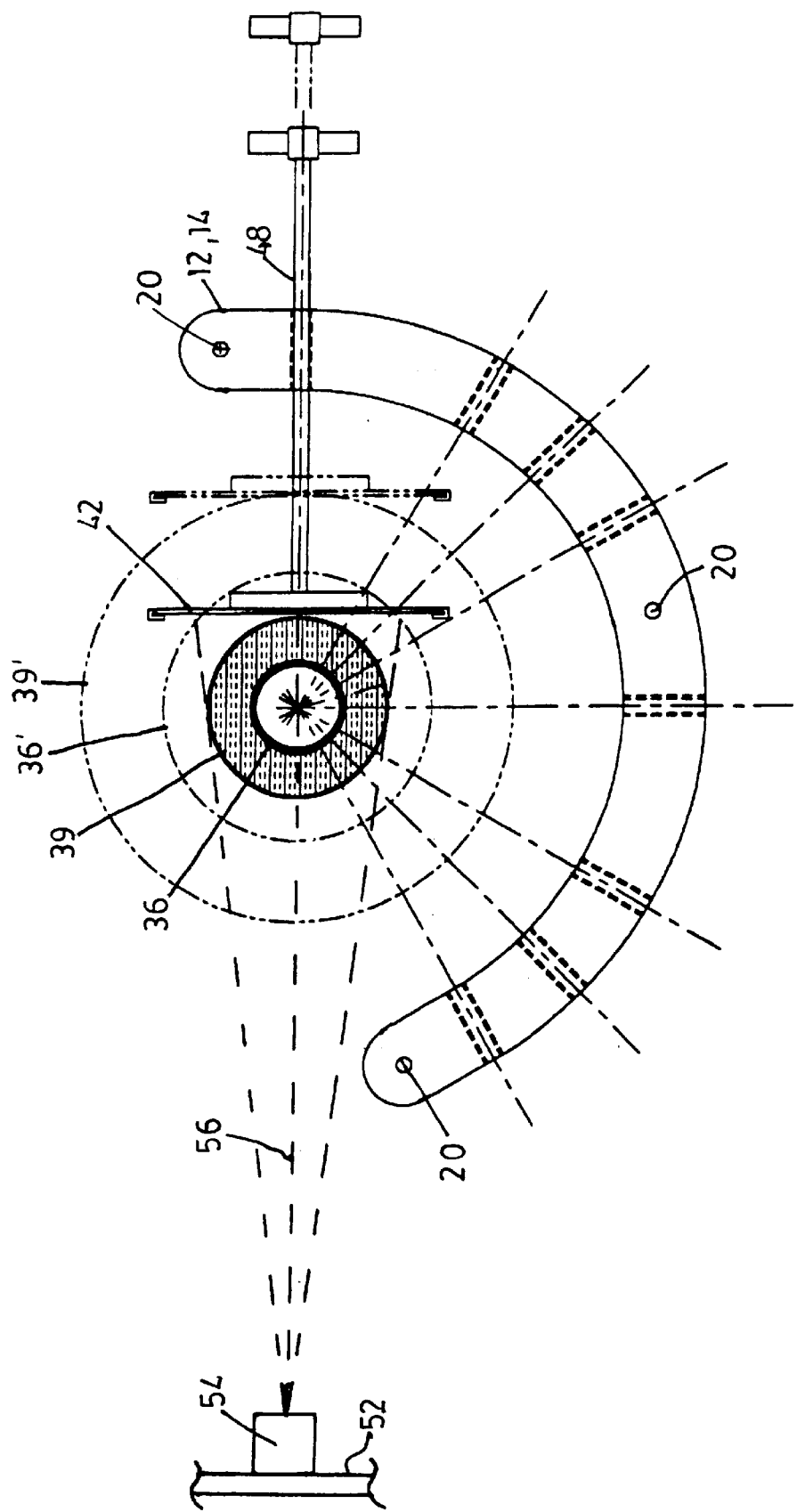
FIG. 4 is an end elevational view, partially in cross-section, of the end piece shown in FIG. 3 supporting a film holder mounted on a pipe for testing.

Supporting framework 11 may be mounted directly onto a concentric pipe covering 39, as shown in FIGS. 1, 2, and 4. Such covering will not affect the radiographic thickness images of the present invention, provided that the pipe covering is not significantly radio-opaque, nor will most liquids being conveyed by a pipe during radiography thereof.

A generally planar film holder 42 is shown in FIGS. 4 through 7 having two spaced apart mounting blocks 44 disposed on the rear surface and having bores 46 for rotatably receiving holder adjustment screws 48 which are threaded through bores 38 in end pieces 12,14. Film holder 42 has upper and lower lips 58,60 creating shallow troughs into which a conventional industrial x-ray film with intensifying screens may be inserted.

Preferably, the length of tubular spacers 18 is such that a single long film sheet can be positioned between end pieces 12,14, although using a separate sheet of film for each exposure is contemplated within the scope of the invention.

Figure 7:
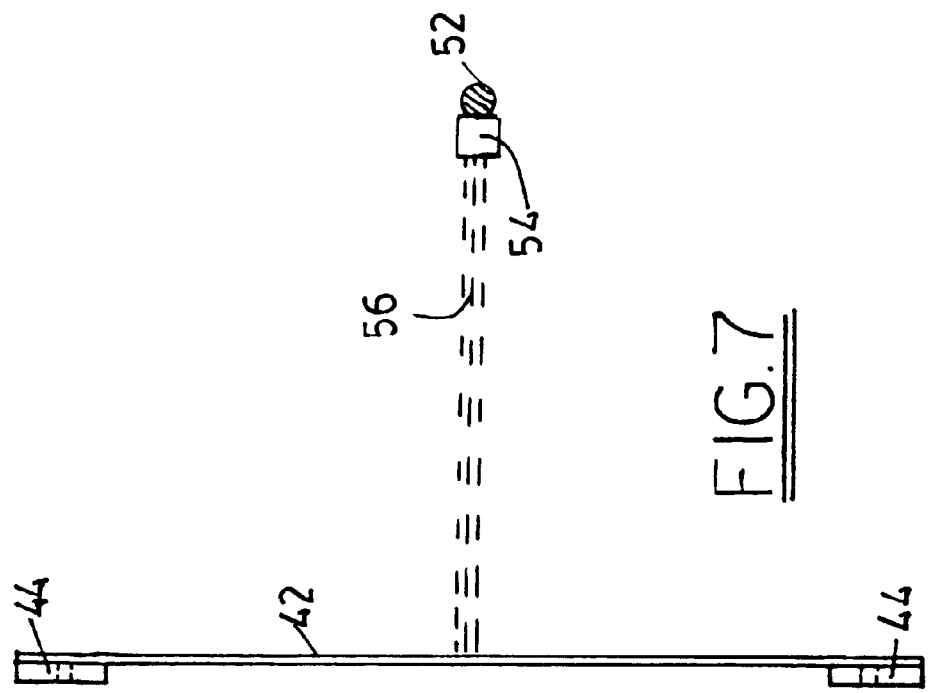
FIG. 7 is a plan view of the film holder-shown in FIG. 4.
Figure 6:
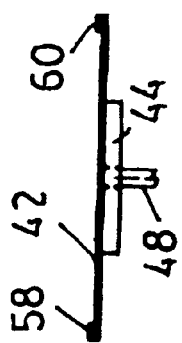
FIG. 6 is a side elevational view of the film holder shown in FIG. 4.
Figure 5:
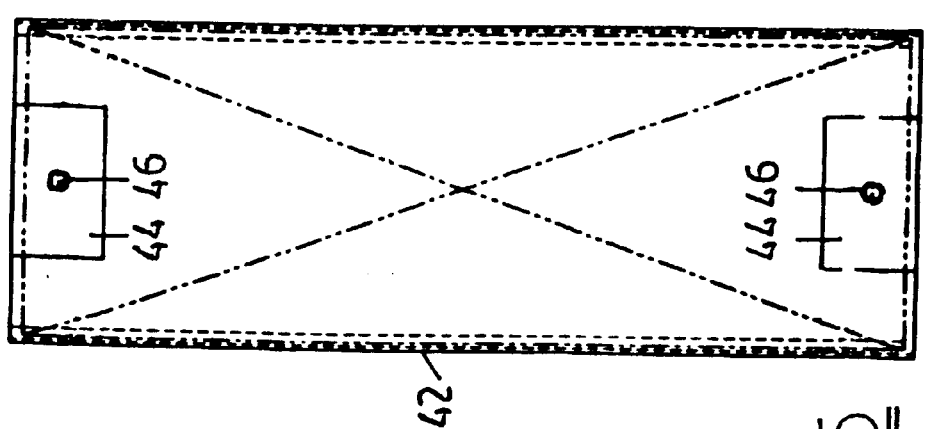

As shown in FIG. 4, off-spaced from film holder 42 is a conventional industrial x-ray source 54 so disposed that the plane of film holder 42 is substantially orthogonal to the centerline beam 56 from source 54 which is coincident with a radius of pipe 36. Thus both holder 42 and source 54 are transected by an axial plane of pipe 36. Source 54 is powered conventionally (not shown) to generate x-rays on demand. Source 54 is provided with a handle 52 for mounting to any convenient support (not shown). Piping to be inspected is very crowded in many industrial installations, and positioning of the source can require flexibility and ingenuity. Thus, no positioning equipment other than handle 52 can be shown. Source 54 emits an axially-narrow beam, as shown in FIG. 7, and a radially broad beam to encompass the entire pipe diameter, as shown in FIG. 8. Thus the apparatus can radiograph a radial (equatorial), or cross-sectional, "slice" of the pipe at a predetermined axial location.

Figure 11:
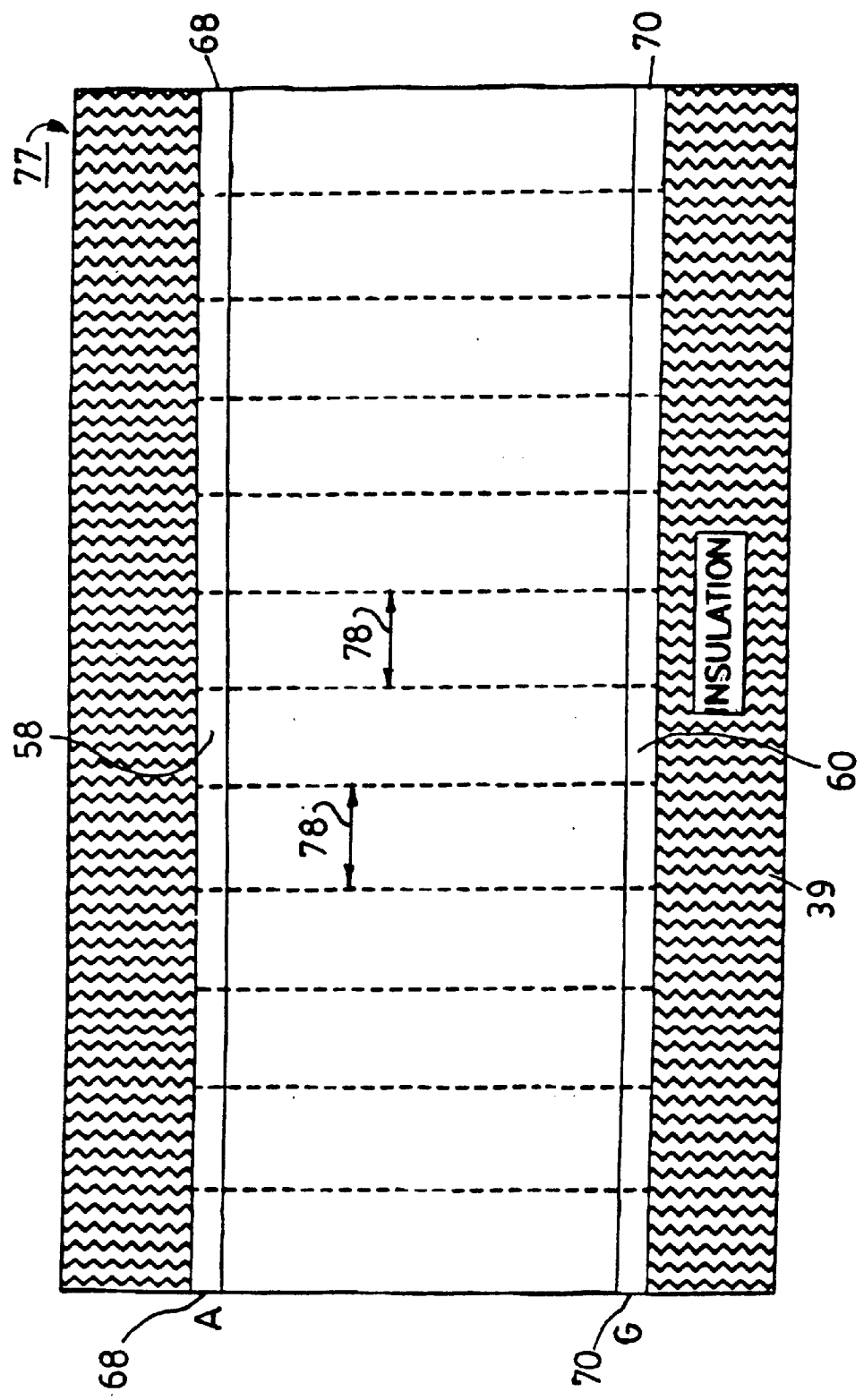
FIG. 11 is a schematic cross-sectional view of pipe walls A and G as taken at radial angle 0°, as shown in FIG. 8b, showing uniform wall thickness.
Figure 12:
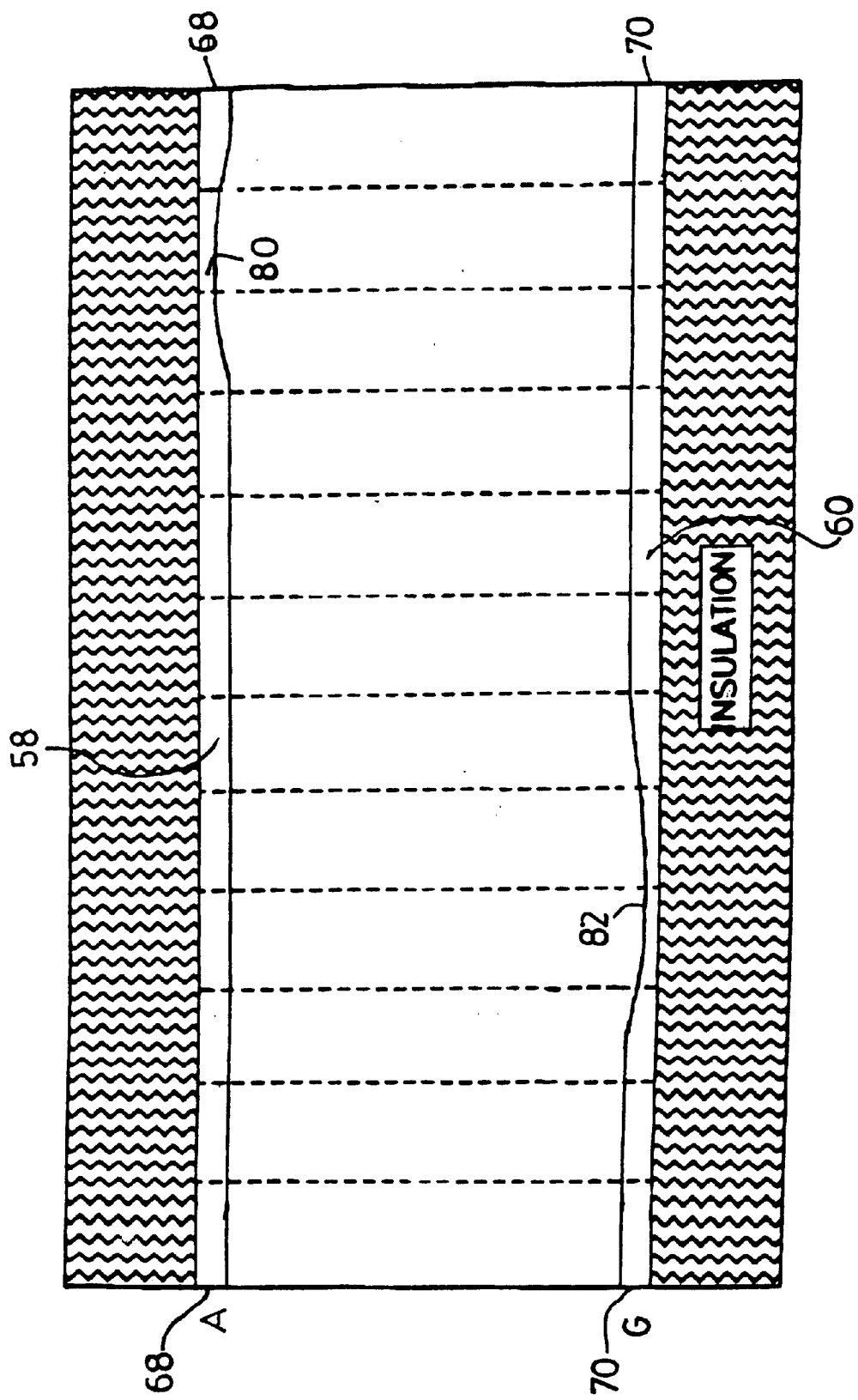
FIG. 12 is a view like that shown in FIG. 11 of another pipe having corrosional thinning of walls A and G.
Figure 13:
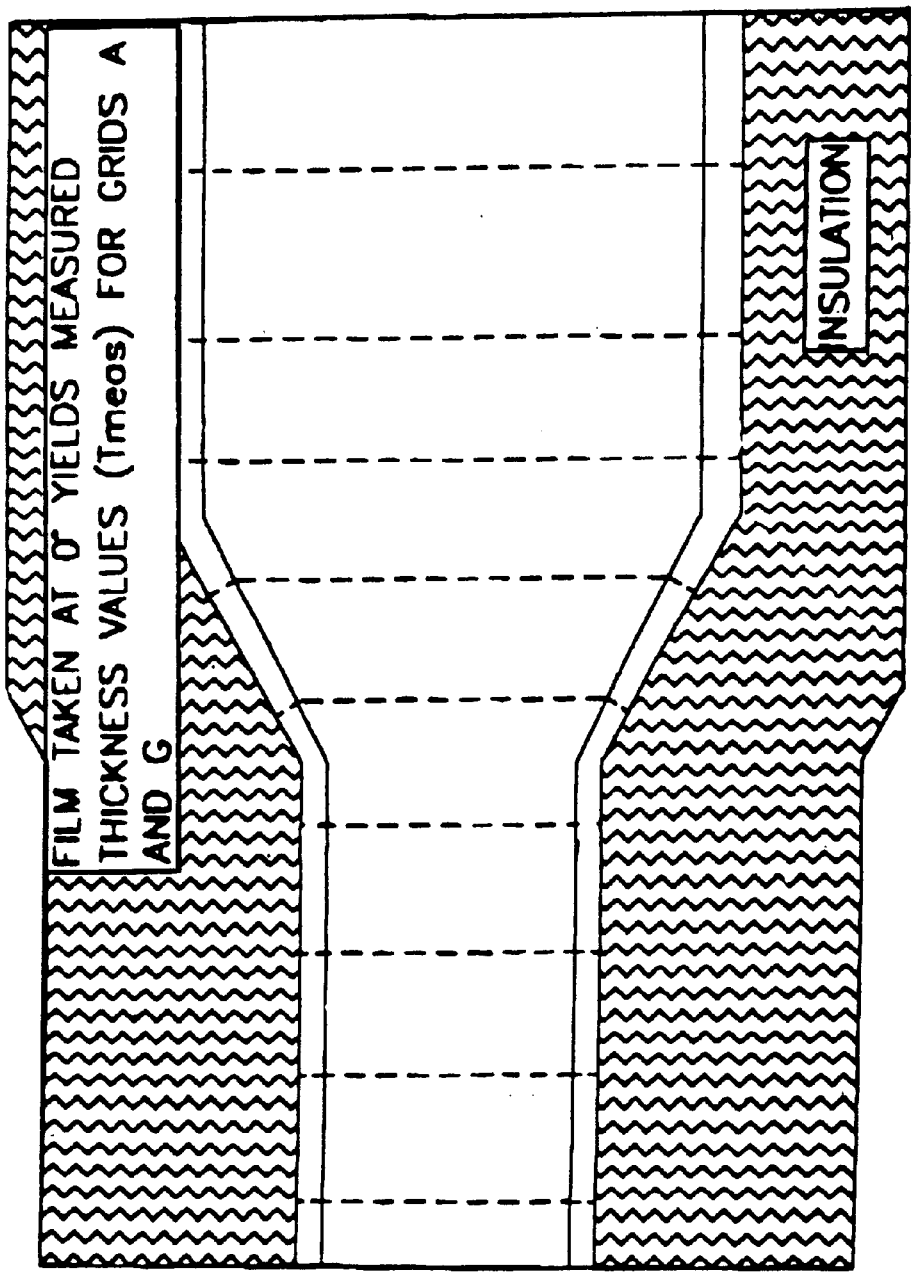
FIG. 13 is a view like that shown in FIG. 11 for a pipe having two diameters and a tapered portion therebetween.
Figure 14:
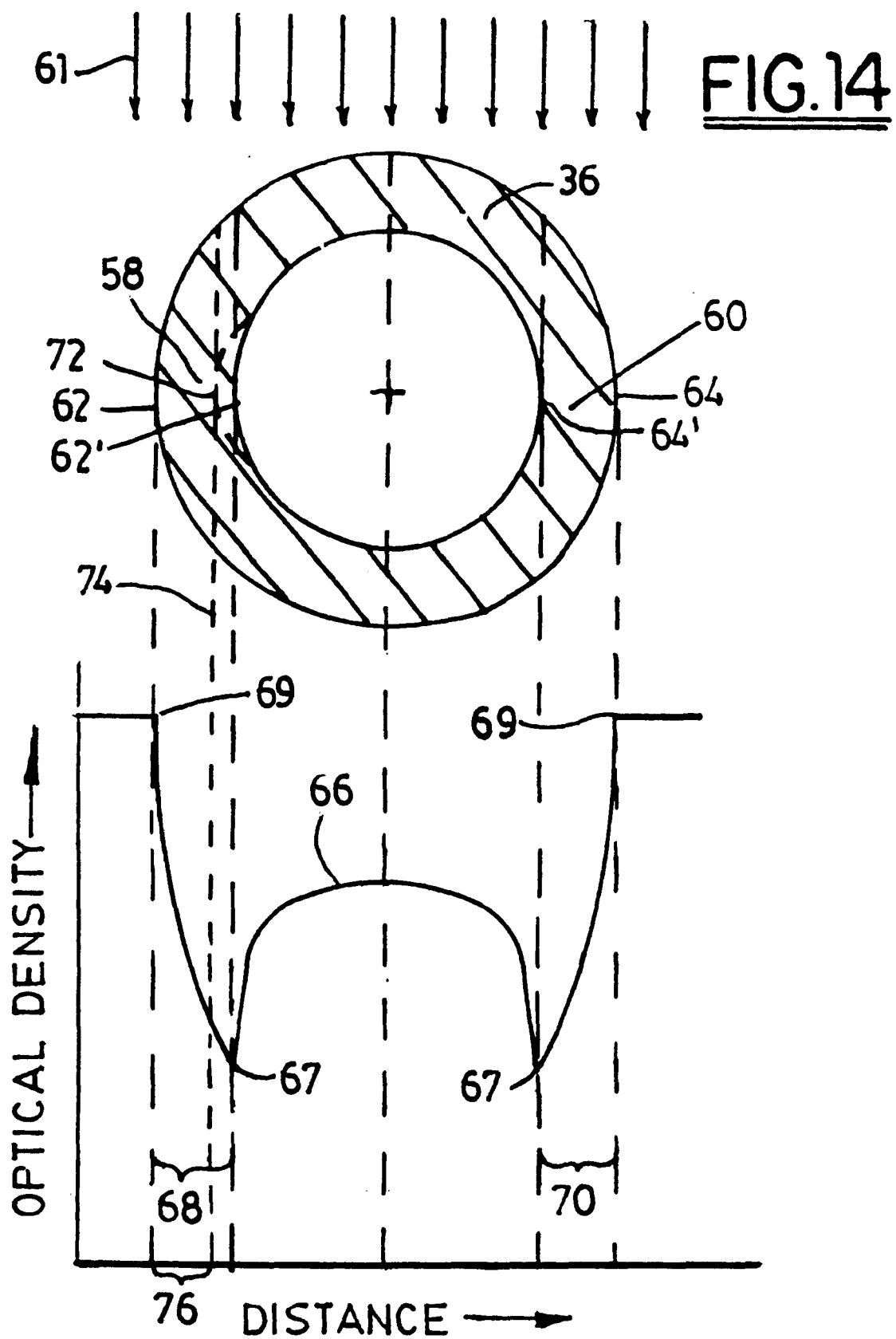
FIG. 14 is a density trace of a radiograph of a pipe taken in accordance with the present invention, showing the sharp. delineation of side wall width.

Source 54 may be positioned stepwise along the axial plane of pipe 36 to radiograph successive cross-sectional slices of the pipe. In each slice, the apparent thicknesses of the upper and lower pipe walls orthogonal to the center beam are determined, as shown in FIG. 14 and discussed in more detail below. Thus, a single radiographic film having multiple adjacent exposures along its length defines a longitudinal axial slice through the pipe, as shown in FIGS. 11 through 13.

Other such slices can be obtained simply by unthreading the holder adjustment screws 48 from the mounting blocks 44 and end pieces 12,14 as shown in FIG. 3, repositioning the film holder 42 at a different radial angle consistent with a different set of threaded radial bores 38, reinserting screws 48 in the new radial bores, installing a fresh sheet of film in film holder 42, and beginning a new axial positioning exposure sequence of source 54. Also, holder 42 may be radially positioned to accommodate different pipe diameters, as shown in FIG. 4, wherein a 2-inch diameter pipe 36 is shown having a 1-inch thick-insulative covering 39, and a 6-inch diameter pipe 36' having a 2-inch thick insulative covering 39' are shown in phantom.

Figure 8A:
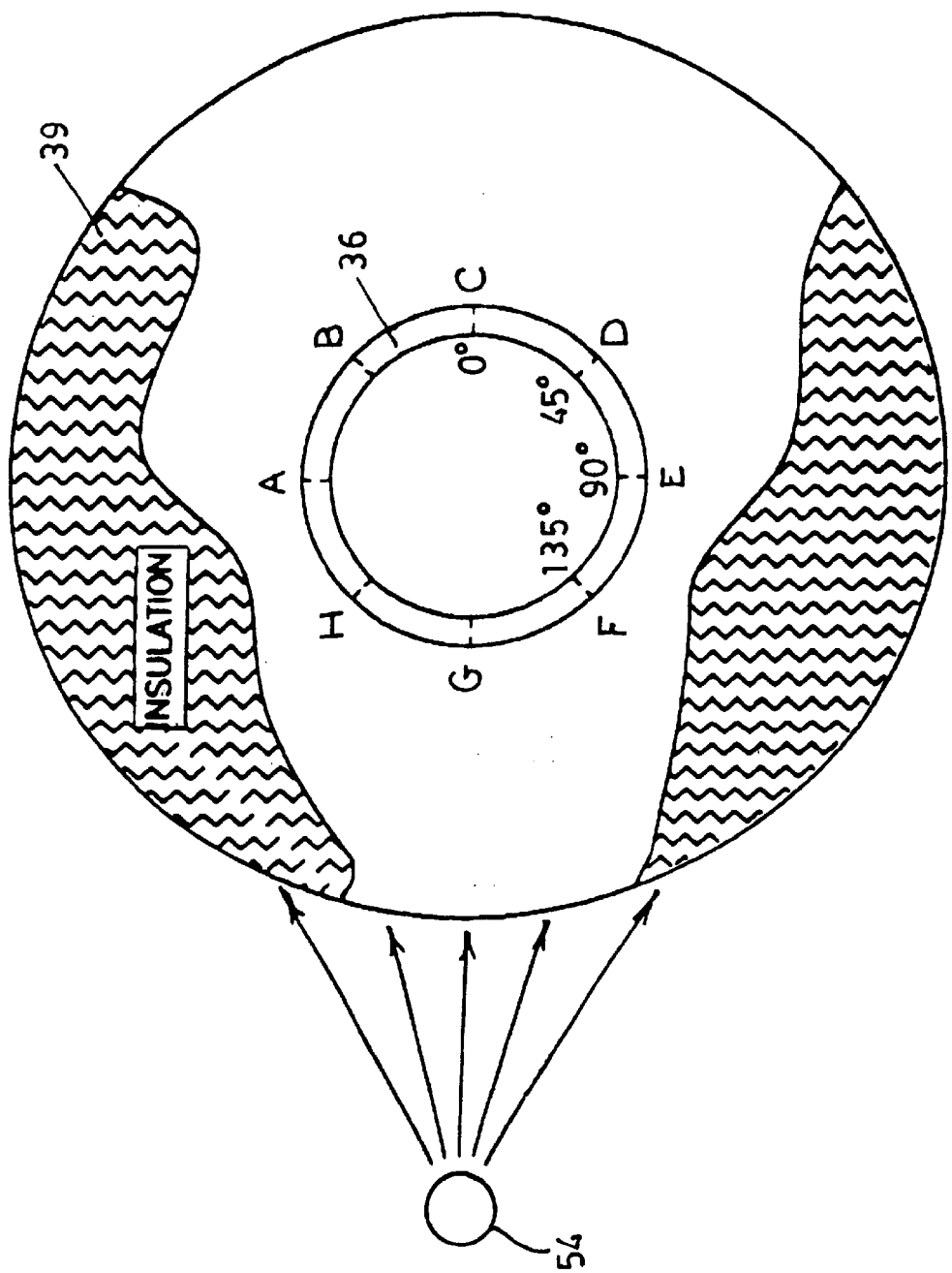
FIG. 8a is a schematic cross-sectional view of an insulation covered 2-inch OD pipe, showing various imaging angles in accordance with the invention.

Referring to FIGS. 8a through 10, the NSAC has specified the spacing of slices along a pipe under test, referred to as "grid size" in FIG. 9, which spacing increases as pipe diameter increases. Further, the required number of radial filming positions is increased as pipe diameter increases. FIG. 8a represents the radial positions for a two-inch OD pipe, requiring four films, as shown in FIG. 9, at four radial angles progressively increasing by 45°, as shown in FIG. 10. FIG. 8b represents the radial positions for a three-inch, four-inch, or six-inch OD pipe, requiring six films, as shown in FIG. 9, at six radial angles progressively increasing by 30°, as shown in FIG. 10.

Referring to FIG. 14, a pipe 36 having a cross-section as shown has a left side wall 58 and right side wall 60. Since the response of the photographic film being used is linear with respect to the intensity of incident radiation 61, the optical density of the film at any distance across the pipe from outer left surface 62 to outer right surface 64 is a simple inverse measure of the thickness of pipe between the film at that distance and the radiation source. Furthermore, in the distance direction, radiation absorption by the pipe changes abruptly at the outer surfaces and at the corresponding inner surfaces 62', 64', resulting in corresponding abrupt changes in the optical density curve 66. Thus-the two minima 67 the two maxima 69 in FIG. 14 clearly indicate the locations of the inner and outer pipe surfaces, and hence the left and right side wall apparent thicknesses 68,70. If the wall is thinned as by corrosion on the inner surface thereof, as suggested by pocket 72 in FIG. 14, the apparent position 74 of the inner wall is shifted to the left showing a left side wall thickness 76 less than right side wall thickness 70.

Figure 8B:
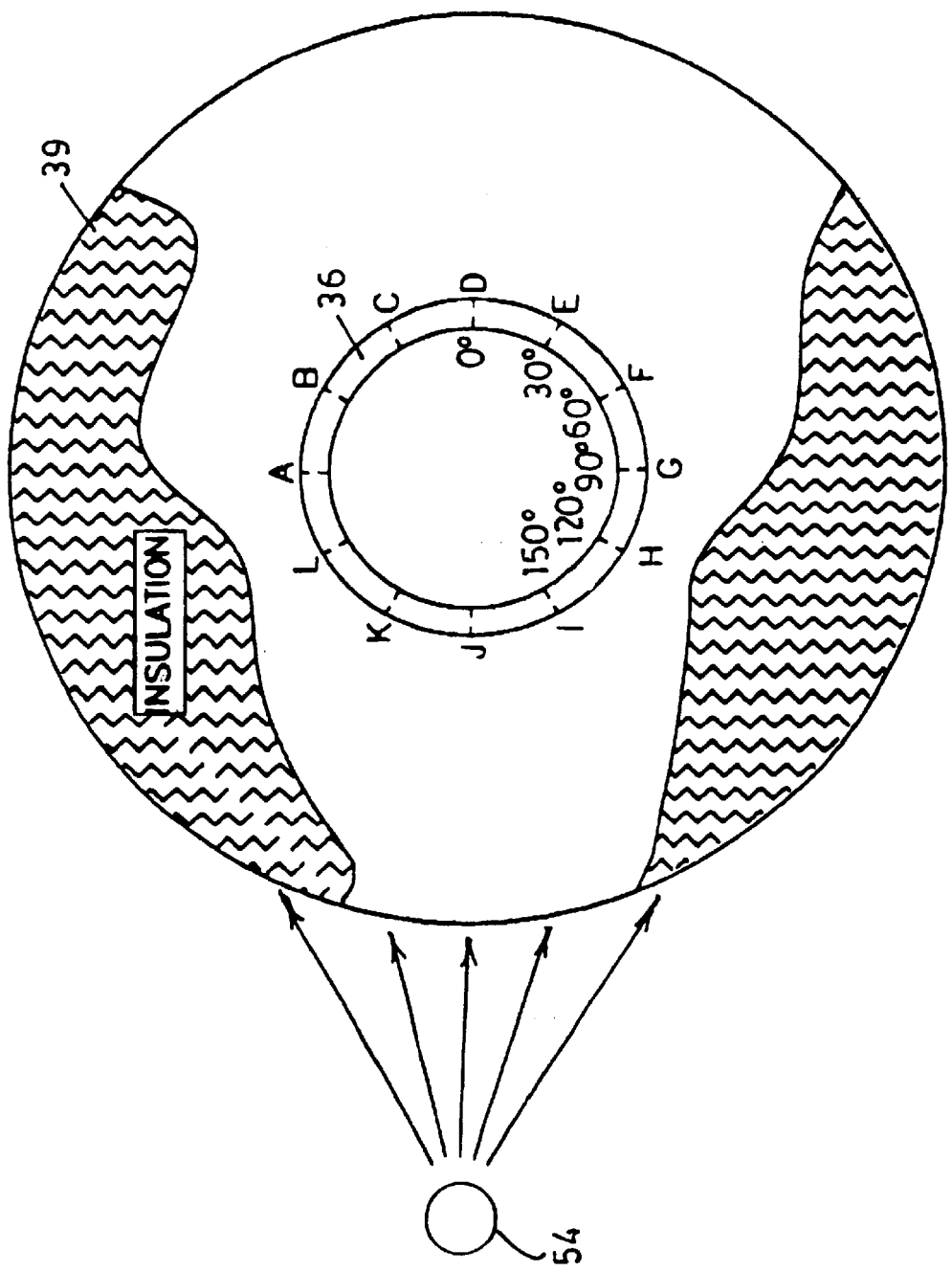
FIG. 8b is a view like FIG. 8a for a 3- to 6-inch OD pipe.

If the x-rays striking the pipe are parallel, as from a linear source, then the measured apparent wall thicknesses are also the true thicknesses. If the x-rays emanate from a point source, as shown in FIGS. 4, 8a, and 8b, and hence are divergent, the true thicknesses may be readily calculated by simple trigonometric relationships, if desired. For example, if the true outside diameter of the pipe is known, the apparent outside diameter can be measured from the radiograph, and the apparent wall thickness can be multiplied by the ratio of the true diameter to the apparent diameter to yield the true wall thickness. However, in many applications the thickness relative to other areas of pipe as measured in the same program is sufficient.

Referring to FIGS. 11 through 13, a longitudinal axial cross-sectional representation 77 of a pipe may be created from a series of exposures taken at the shown grid spacings 78. The axial angle shown in these figures is 0°, as shown in FIGS. 4 and 8b, consequently the measured side walls are at positions A and G. In FIG. 11, the left and right side walls 58,60 are of uniform thickness. In FIG. 12, corrosive thinning of left side wall 58 is seen in area 80, and of right side wall 60 in area 82.

The invention is equally applicable to tapered pipes 84, as shown in FIG. 13.

From the foregoing description it will be apparent that there has been provided an improved system for radiographically measuring in situ pipe wall thickness wherein the side wall thickness is accurately inferable from inflections in an optical density trace of a pipe radiograph. Variations and modifications of the herein described system, in accordance with the invention, will undoubtedly suggest themselves to those skilled in this art. Accordingly, the foregoing description should be taken as illustrative and not in a limiting sense.

What is claimed is:

1. Apparatus for determining the apparent thickness of first and second side walls of a pipe having opposing first and second side walls and opposing front and back walls separating the side walls, comprising:
   a) means for positioning a photographic film along the back wall of said pipe in a plane substantially orthogonal to a first axial plane of said pipe;
   b) means for positioning an x-ray source off-spaced from the front wall of said pipe in said first axial plane in an orientation for radiating x-rays toward said film;
   c) means for processing said film to yield a diametric cross-sectional radiograph of said pipe;
   d) means for measuring optical densities of said radiograph in said diametric direction to determine first and second density maxima corresponding to the outer surfaces of said first and second side walls and first and second density minima corresponding to the respective inner surfaces of said first and second side walls;
   e) means for measuring the diametric distance between said first maximum and minimum to determine the apparent thickness of said first side wall, and between said second maximum and minimum to determine the apparent thickness of said second side wall,
      said means for positioning a photographic film comprising a rigid supporting framework having separate opposed arcuate end pieces, each of said end pieces having at least one threaded radial bore, means for removably attaching said supporting framework to said pipe, and a film holder having adjustment screws extending through said threaded-radial bores in said arcuate end pieces to engage and position said film holder for radiographic exposure.

2. Apparatus in accordance with claim 1 wherein each of said arcuate end pieces is provided with a plurality of said radial bores disposed at predetermined radial angles from each other to permit positioning of said imaging framework in different axial planes corresponding to each of said radial angles.

3. Apparatus in accordance with claim 1 wherein said means for mounting said x-ray,source include means for translating said x-ray source in a direction parallel to said axis of said pipe.

4. A method for radiographically determining the apparent thicknesses of a first side wall and a second side wall of a pipe having opposing first and second side walls and opposing front and back walls separating the side walls, comprising the steps of:

a) disposing a photographic film along said back wall of said pipe;

b) disposing an x-ray source off-spaced from said front wall of said pipe, said source being positioned for radiation of x-rays in an equatorial plane of said pipe toward said film, a first axial plane of said pipe passing through said source and said film;

c) exposing said film to x-rays from said x-ray source;

d) photographically processing said film to form a radiographic image representing a diametric cross-section of said pipe, said diameter being orthogonal to said direction of said radiation;

e) determining a first maximum and a first minimum optical density of said radiographic image and a first spacing therebetween in a direction parallel to said diameter, said first spacing being said apparent thickness of said first side wall;

f) determining a second maximum and a second minimum optical density of said radiographic image and a second spacing therebetween in said direction parallel to said diameter, said second spacing being said apparent thickness of said second side wall;

g) moving said x-ray source stepwise to a plurality of locations in the axial direction of said pipe;

h) performing steps a) through f) at each of said locations, said plurality of exposures at said plurality of locations being made onto a single piece of film.

\* \* \* \* \*